United States Patent
McAnnally et al.

(10) Patent No.: US 10,172,902 B2
(45) Date of Patent: Jan. 8, 2019

(54) OCULAR EYELID SCRUB COMPOSITION FOR THE TREATMENT OF DEMODEX BLEPHARITIS

(71) Applicant: LUNOVUS, LLC, Morris, AL (US)

(72) Inventors: Jeffery McAnnally, Morris, AL (US); John O. Mason, Birmingham, AL (US)

(73) Assignee: Lunovus LLC, Morris, AL (US)

(*) Notice: Subject to any disclaimer, the term of this patent is extended or adjusted under 35 U.S.C. 154(b) by 211 days.

(21) Appl. No.: 15/313,433

(22) PCT Filed: May 26, 2015

(86) PCT No.: PCT/US2015/032411
§ 371 (c)(1),
(2) Date: Nov. 22, 2016

(87) PCT Pub. No.: WO2015/183799
PCT Pub. Date: Dec. 3, 2015

(65) Prior Publication Data
US 2017/0196928 A1    Jul. 13, 2017

Related U.S. Application Data

(60) Provisional application No. 62/003,934, filed on May 28, 2014, provisional application No. 62/040,757, filed on Aug. 22, 2014.

(51) Int. Cl.
| | |
|---|---|
| A61K 36/58 | (2006.01) |
| A61K 36/61 | (2006.01) |
| A61F 9/00 | (2006.01) |
| A61K 36/889 | (2006.01) |
| A61K 9/00 | (2006.01) |
| A61F 9/007 | (2006.01) |
| A61K 47/10 | (2017.01) |
| A61K 47/18 | (2017.01) |
| A61K 47/20 | (2006.01) |
| A61K 47/22 | (2006.01) |
| A61K 47/26 | (2006.01) |
| A61K 47/46 | (2006.01) |

(52) U.S. Cl.
CPC ............ *A61K 36/889* (2013.01); *A61F 9/007* (2013.01); *A61K 9/0048* (2013.01); *A61K 36/58* (2013.01); *A61K 36/61* (2013.01); *A61K 47/10* (2013.01); *A61K 47/18* (2013.01); *A61K 47/20* (2013.01); *A61K 47/22* (2013.01); *A61K 47/26* (2013.01); *A61K 47/46* (2013.01)

(58) Field of Classification Search
CPC .. A61F 9/0017; A61F 9/0026; A61F 9/00718; A61K 36/58; A61K 36/61
See application file for complete search history.

(56) References Cited

U.S. PATENT DOCUMENTS

| | | | |
|---|---|---|---|
| 5,888,984 A | 3/1999 | Brown | |
| 8,128,968 B2 | 3/2012 | Gao et al. | |
| 8,440,240 B2 | 5/2013 | Gao et al. | |
| 8,455,015 B2 | 6/2013 | Gao et al. | |
| 2005/0053680 A1* | 3/2005 | Hopkins | A61K 31/14 424/761 |
| 2008/0274072 A1 | 11/2008 | Manolas et al. | |
| 2012/0014896 A1 | 1/2012 | Dombeck | |
| 2012/0171310 A1* | 7/2012 | Brodie | A61K 9/0017 424/739 |
| 2012/0288575 A1 | 11/2012 | Gilbard et al. | |
| 2013/0224272 A1 | 8/2013 | Gao et al. | |
| 2013/0331768 A1 | 12/2013 | Nichamin | |
| 2013/0344128 A1 | 12/2013 | Gao et al. | |
| 2014/0178444 A1* | 6/2014 | Stadler | C07H 15/04 424/401 |
| 2015/0118165 A1 | 4/2015 | Rudolph et al. | |

OTHER PUBLICATIONS

International Search Report and the Written Opinion of the International Searching Authority issued in PCT/US2015/032411 dated Aug. 18, 2015, 8 pages.

* cited by examiner

*Primary Examiner* — Susan S Su
(74) *Attorney, Agent, or Firm* — Burr & Forman LLP; Harvey S. Kauget

(57) ABSTRACT

A composition for the treatment of *Demodex* blepharitis containing tea tree oil and/or Neem oil and coconut oil in glycerol or in water or in a mixture of glycerol and water. The composition may further contain *aloe barbadensis* gel, sodium lauryl sulfate, cocoamidopropyl betaine, lauroyl glucoside, or DMDM hydantoin, or a combination thereof, in glycerol or in water or in a mixture of glycerol and water. The composition is used to treat *Demodex* blepharitis by applying the composition to the eyelid margin and eyelashes and scrubbing the eyelid margin, eyelashes, and eyelash roots with the composition using any suitable cloth, wipe, sponge, brush, or cotton tipped applicator.

10 Claims, No Drawings

OCULAR EYELID SCRUB COMPOSITION FOR THE TREATMENT OF DEMODEX BLEPHARITIS

TECHNICAL FIELD

The present invention relates to methods and compositions for treating ocular *Demodex*, *Demodex*-induced blepharitis, and meibomian gland dysfunction and, more particularly, to the use of tea tree oil and/or Neem oil, in combination with coconut oil, on the eyelid, eyelashes, and eyelash roots.

BACKGROUND ART

*Demodex* (class Arachnida, superorder Acariformes) is one of the most commonly found ectoparasites in humans. On the eyelids, *D. folliculorum* lives in the eyelash follicles and *D. brevis* lives deep in the meibomian glands and the sebaceous glands of the lashes. They eat skin cells, and oils in the hair follicle. It is reported that *Demodex* is an etiologic factor in chronic blepharitis, conjunctival inflammation, and meibomian gland dysfunction. Patients who suffer from blepharitis as a result of an ocular *Demodex* infestation often present a number of symptoms such as foreign body sensation in the eye, redness, and itching. Uncontrolled ocular *Demodex* infestation in eyelids may cause mal-directed eye lashes (trichiasis), meibomian gland dysfunction leading to lipid tear deficient dry eye, conjunctival inflammation (conjunctivitis), and sight-threatening corneal abnormalities. The symptoms can become severe enough that the patient may require surgery to achieve relief.

Tea tree oil (TTO) is natural oil distilled from the leaf of *Melaleuca alternifolia*. TTO is known to be effective for killing *Demodex* in vitro and in vivo. A lid scrubbing treatment with TTO is known to be effective for decreasing *Demodex* in eyelashes treated with a cotton tip wetted with 10% TTO (Koo et al, J Korean Med Sci 2012; 27: 1574-1579). One of the active components of TTO is terpinen-4-ol. U.S. Pat. No. 8,455,015 discloses that terpinen-4-ol is effective in treating an ocular *Demodex* infestation or *Demodex*-induced blepharitis in the form of solutions, suspensions, sprays, lotions, gels, pastes, medicated sticks, balms, cleansers (including shampoos and soaps), creams, or ointments.

Neem oil is a natural oil pressed from the fruits and seeds of the Neem tree (*Azadirachta indica*). Neem oil is known to be an effective miticide for killing various forms of mites. A component of Neem oil, azadirachtin, works by interfering with the hormone systems of mites to hinder their ability to feed, grow, molt, and reproduce. Once the *Demodex* mites have been exposed to Neem oil their life cycle is broken and their population will decrease. Although Neem oil is a miticide, it is not known to be useful in the treatment of *Demodex* blepharitis.

DISCLOSURE OF THE INVENTION

This invention provides a composition for the treatment of *Demodex* blepharitis containing tea tree oil (TTO), 0.1-10% v/v, and/or Neem oil, 0.1-95% v/v, and coconut oil, 1-10% v/v, in glycerol or in water or in a mixture of glycerol and water. The composition may further contain *aloe barbadensis* gel, 0.1 to 10% v/v, sodium lauryl sulfate, 0.5 to 5%, w/v, cocoamidopropyl betaine, 0.1 to 5% v/v, lauroyl glucoside, 1% to 10% w/v, or DMDM hydantoin, 0.1 to 5% v/v, or a combination thereof, in glycerol or in water or in a mixture of glycerol and water.

This invention further provides a method for treating *Demodex* blepharitis. The composition described above is provided to a subject having *Demodex* blepharitis. The composition is applied to the eyelid margin and eyelashes. The eyelid margin, eyelashes, and eyelash roots are scrubbed with the composition. Any suitable cloth, wipe, sponge, brush, or cotton tipped applicator may be used for scrubbing.

An advantage of this invention is the combination of TTO and coconut oil which improves the effectiveness of TTO in relieving the symptoms and progression of *Demodex* blepharitis.

Another advantage is the use of the mitocide Neem oil to treat the symptoms and progression of *Demodex* blepharitis.

Another advantage is the combination of TTO and Neem oil in coconut oil to provide a further improvement in the treatment of symptoms and progression of *Demodex* blepharitis.

BEST MODES FOR CARRYING OUT THE INVENTION

While the following description details the preferred embodiments of the present invention, it is to be understood that the invention is not limited in its application to the details of the disclosures and descriptions in the accompanying specification, since the invention is capable of other embodiments and of being practiced in various ways.

The present invention provides an increased, improved effectiveness of tea tree oil (TTO) or Neem oil, or a combination thereof, on the eyelid by combining these compounds with coconut oil. Coconut oil is active as an anti-microbial and moisturizer. Addition of other key ingredients can further improve the effectiveness of tea tree TTO and/or Neem oil on the eyelid. TTO is formulated at 0.1-10%, preferably 1%, v/v, Neem oil is formulated at 0.1-95%, preferably 10%, v/v, and coconut oil is formulated at 1-10%, preferably 3%, v/v, in substances such as glycerol or water or a mixture of glycerol and water. Other ingredients that can be combined with TTO and/or Neem oil and coconut oil are *aloe barbadensis* gel, 0.1 to 10% v/v; sodium lauryl sulfate, 0.5 to 5%, w/v; cocoamidopropyl betaine, 0.1 to 5% v/v; lauroyl glucoside 1% to 10% w/v; and DMDM hydantoin 0.1 to 5% v/v.

Example 1

1 ml of TTO and 3 ml of coconut oil are added to 80 ml of glycerol and 16 ml of water to provide 1% v/v TTO and 3% coconut oil v/v in a mixture of glycerol 80% v/v and water 16% v/v.

Example 2

10 ml of Neem oil and 3 ml of coconut oil are added to 70 ml of glycerol and 17 ml of water to provide 10% v/v Neem oil and 3% coconut oil v/v in a mixture of glycerol 70% v/v and water 13%.

Example 3

1 ml of TTO, 10 ml of Neem oil; and 3 ml of coconut oil are added to 69 ml of glycerol and 17 ml of water to provide 1% v/v TTO, 10% v/v Neem oil, 3% v/v coconut oil in a mixture of glycerol 69% v/v and water 17% v/v.

Example 4

1% v/v TTO and 3% coconut oil v/v are combined with *aloe barbadensis* gel, 0.1 to 10% v/v; sodium lauryl sulfate, 0.5 to 5%, w/v; cocoamidopropyl betaine, 0.1 to 5% v/v; lauroyl glucoside 1% to 10% w/v; or DMDM hydantoin 0.1 to 5% v/v, or a combination thereof, in glycerol or water or any desired mixture of glycerol and water.

Example 5

10% v/v Neem oil and 3% coconut oil v/v are combined with *aloe barbadensis* gel, 0.1 to 10% v/v; sodium lauryl sulfate, 0.5 to 5%, w/v; cocoamidopropyl betaine, 0.1 to 5% v/v; lauroyl glucoside 1% to 10% w/v; or DMDM hydantoin 0.1 to 5% v/v, or a combination thereof, in glycerol or water or any desired mixture of glycerol and water.

Example 6

1% v/v TTO, 10% v/v Neem oil, and 3% v/v coconut oil in a mixture of glycerol 69% v/v and water 17% v/v are combined with *aloe barbadensis* gel, 0.1 to 10% v/v; sodium lauryl sulfate, 0.5 to 5%, w/v; cocoamidopropyl betaine, 0.1 to 5% v/v; lauroyl glucoside 1% to 10% w/v; or DMDM hydantoin 0.1 to 5% v/v, or a combination thereof, in glycerol or water or any desired mixture of glycerol and water.

Formulations and compositions of TTO and/or Neem oil and coconut oil can be used in combination with cleaning towels or cotton tipped applicators for application of the formulation to the eyelid. The formulations and compositions can also be prepared in a foam dispensing bottle having a pharmaceutical foam composition comprising water, a hydrophobic solvent, a surface-active agent, or a gelling agent, or a combination thereof, and a propellant.

The formulations and compositions of TTO and/or Neem oil and coconut oil provide a method of treating an ocular *Demodex*-induced blepharitis in the eyelid. The method includes administering to the eyelid a therapeutically-effective amount of a composition having TTO or Neem oil, or a combination thereof, and coconut oil as active agents. The composition is administered topically to the eyelid margin and eyelashes by means of a cleaning towel, a cotton tip applicator, or a foam composition, or a combination thereof. The eyelid margin, eyelashes, and eyelash roots are scrubbed with the composition.

Example 7

A composition having TTO or Neem oil, or a combination thereof, and coconut oil as active agents is provided to a person having *Demodex*-induced blepharitis in the eyelid. The composition is applied to the eyelid margin and eyelashes. The eyelid margin, eyelashes, and eyelash roots are scrubbed with the composition using any suitable cloth, wipe, sponge, brush, or cotton tipped applicator.

While this invention has been described in some detail with reference to specific exemplary embodiments, there is no intention that the invention be limited to such detail. On the contrary, the invention is intended to include any alternative or equivalent embodiments that fall within the spirit and scope of the invention as described and claimed herein.

The invention claimed is:

1. A composition for the treatment of *Demodex* blepharitis, comprising: tea tree oil (TTO), 0.1-10% v/v, or Neem oil, 0.1-95% v/v, coconut oil, 1-10% v/v, *aloe barbadensis* gel, 0.1 to 10% v/v, sodium lauryl sulfate, 0.5 to 5%, w/v, cocoamidopropyl betaine, 0.1 to 5% v/v, lauroyl glucoside, 1% to 10% w/v, or DMDM hydantoin, 0.1 to 5% v/v, or a combination thereof, in glycerol or in water or in a mixture of glycerol and water.

2. A composition for the treatment of *Demodex* blepharitis, comprising: tea tree oil (TTO), 0.1-10% v/v, or Neem oil, 0.1-95% v/v, coconut oil, 1-10% v/v, *aloe barbadensis* gel, 0.1 to 10% v/v, sodium lauryl sulfate, 0.5 to 5% w/v, cocoamidopropyl betaine, 0.1 to 5% v/v, lauroyl glucoside, 1% to 10% w/v, and DMDM hydantoin, 0.1 to 5% v/v, in glycerol or in water or in a mixture of glycerol and water.

3. A composition for the treatment of *Demodex* blepharitis, comprising: tea tree oil (TTO), 0.1-10% v/v, and Neem oil, 0.1-95% v/v, and coconut oil, 1-10% v/v, *aloe barbadensis* gel, 0.1 to 10% v/v, sodium lauryl sulfate, 0.5 to 5%, w/v, cocoamidopropyl betaine, 0.1 to 5% v/v, lauroyl glucoside 1% to 10% w/v, or DMDM hydantoin 0.1 to 5% v/v, or a combination thereof, in glycerol or in water or in a mixture of glycerol and water.

4. A composition for the treatment of *Demodex* blepharitis, comprising: tea tree oil (TTO), 0.1-10% v/v, and Neem oil, 0.1-95% v/v, and coconut oil, 1-10% v/v, *aloe barbadensis* gel, 0.1 to 10% v/v, sodium lauryl sulfate, 0.5 to 5% w/v, cocoamidopropyl betaine, 0.1 to 5% v/v, lauroyl glucoside, 1% to 10% w/v, and DMDM hydantoin, 0.1 to 5% v/v, in glycerol or in water or in a mixture of glycerol and water.

5. A method for treating *Demodex* blepharitis, comprising the steps of: 1) providing a composition comprising tea tree oil (TTO), 0.1-10% v/v, or Neem oil, 0.1-95% v/v, and coconut oil, 1-10% v/v, in glycerol or in water or in a mixture of glycerol and water; 2) applying said composition to the eyelid margin and eyelashes; and 3) scrubbing the eyelid margin, eyelashes, and eyelash roots with said composition using any suitable cloth, wipe, sponge, brush, or cotton tipped applicator.

6. The method of claim 5, wherein said composition further comprises: *aloe barbadensis* gel, 0.1 to 10% v/v, sodium lauryl sulfate, 0.5 to 5%, w/v, cocoamidopropyl betaine, 0.1 to 5% v/v, lauroyl glucoside, 1% to 10% w/v, or DMDM hydantoin, 0.1 to 5% v/v, or a combination thereof, in glycerol or in water or in a mixture of glycerol and water.

7. The method of claim 5, wherein said composition further comprises: *aloe barbadensis* gel, 0.1 to 10% v/v, sodium lauryl sulfate, 0.5 to 5% w/v, cocoamidopropyl betaine, 0.1 to 5% v/v, lauroyl glucoside, 1% to 10% w/v, and DMDM hydantoin, 0.1 to 5% v/v, in glycerol or in water or in a mixture of glycerol and water.

8. A method for treating *Demodex* blepharitis, comprising the steps of: 1) providing a composition comprising: tea tree oil (TTO), 0.1-10% v/v, and Neem oil, 0.1-95% v/v, and coconut oil, 1-10% v/v, in glycerol or in water or in a mixture of glycerol and water; 2) applying said composition to the eyelid margin and eyelashes; and 3) scrubbing the eyelid margin, eyelashes, and eyelash roots with said composition using any suitable cloth, wipe, sponge, brush, or cotton tipped applicator.

9. The method of claim 8, wherein said composition further comprises: *aloe barbadensis* gel, 0.1 to 10% v/v, sodium lauryl sulfate, 0.5 to 5%, w/v, cocoamidopropyl betaine, 0.1 to 5% v/v, lauroyl glucoside 1% to 10% w/v, or DMDM hydantoin 0.1 to 5% v/v, or a combination thereof, in glycerol or in water or in a mixture of glycerol and water.

10. The method of claim 8, wherein said composition further comprises: *aloe barbadensis* gel, 0.1 to 10% v/v, sodium lauryl sulfate, 0.5 to 5% w/v, cocoamidopropyl betaine, 0.1 to 5% v/v, lauroyl glucoside, 1% to 10% w/v, and DMDM hydantoin, 0.1 to 5% v/v, in glycerol or in water or in a mixture of glycerol and water.

\* \* \* \* \*